United States Patent
Treskow et al.

(10) Patent No.: US 11,912,648 B2
(45) Date of Patent: Feb. 27, 2024

(54) METHOD FOR PREPARING C-H ACIDIC (METH)ACRYLATES

(71) Applicant: EVONIK OPERATIONS GMBH, Essen (DE)

(72) Inventors: Marcel Treskow, Darmstadt (DE); Maik Caspari, Alsbach-Haehnlein (DE); Thorben Schütz, Alsbach-Hähnlein (DE); Steffen Krill, Mühltal (DE)

(73) Assignee: Evonik Operations GmbH, Essen (DE)

( * ) Notice: Subject to any disclaimer, the term of this patent is extended or adjusted under 35 U.S.C. 154(b) by 435 days.

(21) Appl. No.: 17/260,226

(22) PCT Filed: Jul. 10, 2019

(86) PCT No.: PCT/EP2019/068485
§ 371 (c)(1),
(2) Date: Jan. 14, 2021

(87) PCT Pub. No.: WO2020/016071
PCT Pub. Date: Jan. 23, 2020

(65) Prior Publication Data
US 2021/0269393 A1 Sep. 2, 2021

(30) Foreign Application Priority Data
Jul. 17, 2018 (EP) .................... 18183907

(51) Int. Cl.
*C07C 253/30* (2006.01)
*C07C 253/34* (2006.01)

(52) U.S. Cl.
CPC .......... *C07C 253/30* (2013.01); *C07C 253/34* (2013.01)

(58) Field of Classification Search
None
See application file for complete search history.

(56) References Cited

U.S. PATENT DOCUMENTS

| | | | |
|---|---|---|---|
| 3,272,855 A | 9/1966 | Stobel et al. | |
| 3,642,877 A | 2/1972 | Jayawant | |
| 3,850,988 A | 11/1974 | Ruby | |
| 4,215,195 A | 7/1980 | Ponticello et al. | |
| 4,416,964 A | 11/1983 | Nobuhiro et al. | |
| 4,672,105 A | 6/1987 | Schlosser et al. | |
| 4,745,213 A | 5/1988 | Schlosser et al. | |
| 5,395,892 A | 3/1995 | Haeberle et al. | |
| 5,888,481 A | 3/1999 | Horn et al. | |
| 6,008,404 A | 12/1999 | Miller et al. | |
| 6,706,910 B2 | 3/2004 | Iwakura et al. | |
| 8,420,709 B2 | 4/2013 | Breiner et al. | |
| 8,669,328 B2 | 3/2014 | Breiner et al. | |
| 8,742,163 B2 | 6/2014 | Knebel et al. | |
| 9,162,976 B2 | 10/2015 | Richard et al. | |
| 9,512,062 B2 | 12/2016 | Knebel et al. | |
| 9,656,941 B2 | 5/2017 | Kleese et al. | |
| 10,343,980 B2 | 7/2019 | Krill et al. | |
| 10,407,701 B2 | 9/2019 | Kim et al. | |
| 10,935,695 B2 | 3/2021 | Mahadevan et al. | |
| 11,319,276 B2 | 5/2022 | Treskow et al. | |
| 11,414,373 B2 | 8/2022 | Hartmann et al. | |
| 11,505,520 B2 | 11/2022 | Bleith et al. | |
| 11,512,043 B2 | 11/2022 | Treskow et al. | |
| 2005/0277716 A1 | 12/2005 | Pearson et al. | |
| 2005/0277759 A1 | 12/2005 | Pearson et al. | |
| 2006/0142408 A1 | 6/2006 | Liu et al. | |
| 2008/0234515 A1* | 9/2008 | Liu ..................... | C07C 231/02 564/135 |
| 2011/0196169 A1 | 8/2011 | Knebel et al. | |
| 2011/0218312 A1 | 9/2011 | Knebel et al. | |
| 2014/0221591 A1 | 8/2014 | Nguyen et al. | |
| 2014/0288330 A1 | 9/2014 | Broell et al. | |
| 2016/0297738 A1 | 10/2016 | Klesse et al. | |
| 2019/0271798 A1* | 9/2019 | Mahadevan ......... | C08F 283/12 |
| 2019/0352251 A1 | 11/2019 | Hartmann et al. | |
| 2020/0331845 A1 | 10/2020 | Treskow et al. | |
| 2021/0163439 A1 | 6/2021 | Treskow et al. | |
| 2021/0179529 A1 | 6/2021 | Treskow et al. | |
| 2021/0179531 A1 | 6/2021 | Treskow et al. | |
| 2021/0214297 A1 | 7/2021 | Bleith et al. | |
| 2021/0332005 A1 | 10/2021 | Treskow et al. | |
| 2022/0056005 A9 | 2/2022 | Treskow et al. | |
| 2022/0112154 A1 | 4/2022 | Treskow et al. | |

FOREIGN PATENT DOCUMENTS

| | | |
|---|---|---|
| CA | 1340884 | 1/2000 |
| CN | 1360605 | 7/2002 |
| CN | 103173138 | 6/2013 |
| EA | 201501099 | 7/2016 |
| EP | 0016518 | 10/1980 |
| EP | 2246403 | 11/2010 |

(Continued)

OTHER PUBLICATIONS

CAS Registry No. 1901377-28-3; STN on the Web Registry database; Chemical Abstract RN; dated Dec. 6, 2022.
CAS Registry No. 1909213-39-3; STN on the Web Registry database; Chemical Abstract RN; dated Dec. 6, 2022.
Airgas: Methylamines (downloaded on Mar. 8, 2022 from https://web.archive.org/web/20160302072912/http://airgasspecialtyproducts.com/products/methylamines/; originally captured by the Wayback Machine on Mar. 2, 2016).
Paulsen, et al.,"Efficient and scalable synthesis of α,α-disubstituted β-amino amides," *Organic & Biomolecular Chemistry* 14(31):7570-7578 (2016).
International Search Report for corresponding international application PCT/EP2019/068485, filed Jul. 10, 2019.
Written Opinion of the International Searching Autjority for corresponding international application PCT/EP2019/068485, filed Jul. 10, 2019.

(Continued)

*Primary Examiner* — Joseph R Kosack
(74) *Attorney, Agent, or Firm* — Law Office of Michael A. Sanzo, LLC

(57) ABSTRACT

The invention relates to a method for preparing C—H acidic (meth)acrylates and the uses thereof.

12 Claims, No Drawings

(56) References Cited

FOREIGN PATENT DOCUMENTS

| | | |
|---|---|---|
| GB | 1193412 | 6/1970 |
| GB | 2162 516 | 2/1986 |
| GB | 2248234 | 4/1992 |
| JP | 2000-292887 | 10/2000 |
| JP | 2003261506 | 9/2003 |
| SU | 234254 | 1/1969 |
| TW | 201807491 | 3/2018 |
| WO | WO 2009/146995 | 12/2009 |
| WO | WO 2010/021956 | 2/2010 |
| WO | WO 2012/084737 | 6/2012 |
| WO | WO 2017/145022 | 8/2017 |
| WO | WO 2017/147040 | 8/2017 |

OTHER PUBLICATIONS

International Preliminary Report on Patentability for corresponding international application PCT/EP2019/068485, filed Jul. 10, 2019.
European Search Report Search Opinion for corresponding European application EP 18 18 3907 filed Jul. 17, 2018 with English language machine translation of the Search Opinion attached.
International Search Report for international application PCT/EP2019/068206, filed Jul. 8, 2019; corresponding to copending U.S. Appl. No. 17/260,223.
Written Opinion of the International Searching Autjority for international application PCT/EP2019/068206, filed Jul. 8, 2019; corresponding to copending U.S. Appl. No. 17/260,223.
International Preliminary Report on Patentability for international application PCT/EP2019/068206, filed Jul. 8, 2019; corresponding to copending U.S. Appl. No. 17/260,223.
European Search Report Search Opinion for European application EP 18 18 3897 filed Jul. 17, 2018 with English language machine translation of the Search Opinion attached; corresponding to copending U.S. Appl. No. 17/260,223.
Casas, et al., "Kinetics of chemical interesterification of sunflower oil with methyl acetate for biodiesel and triacetin production," *Chemical Engineering Journal* 171:1324-1332 (2011).
O' Donnell, et al., "Microstructure, Kinetics, and Transport in Oil-in-Water Microemulsion Polymerizations," *Macromolecular Rapid Communications* 28(14):1445-1454 (2007).
U.S. Appl. No. 16/753,287filed Apr. 2, 2020, US-2020/0331845 A2, Oct. 22, 2020, Treskow.
U.S. Appl. No. 16/479,497, filed Jul. 9, 2019, US-2019/0352251 A1, Nov. 21, 2019, Hartmann.
U.S. Appl. No. 16/973,995, Dec. 10, 20201, Treskow.
U.S. Appl. No. 17/057,659, filed Nov. 21, 2020, Bleith.
U.S. Appl. No. 17/260,223, filed Jan. 14, 2021, Treskow.
U.S. Appl. No. 17/262,735, filed Jan. 24, 2021, Treskow.
U.S. Appl. No. 17/268,463, filed Feb. 13, 2021, Treskow.
U.S. Appl. No. 17/268,465, filed Feb. 13, 2021, Treskow.
English language machine translation of Japanese patent reference JP06175252 (published Jun. 24, 1994).
English language machine translation of Japanese patent reference JP06250351 (published Sep. 9, 1994).
English language machine translation of Japanese patent reference JP2008058781 (published Mar. 13, 2008).

* cited by examiner

METHOD FOR PREPARING C—H ACIDIC (METH)ACRYLATES

CROSS REFERENCE TO RELATED APPLICATIONS

The present application is US national stage of international application PCT/EP2019/068485, which had an international filing date of Jul. 10, 2019 and which was published on Jan. 23, 2020. The application claims priority to EP 18183907.7, filed on Jul. 17, 2018. The contents of the priority application is hereby incorporated by reference in its entirety.

The invention relates to a method for preparing C—H acidic (meth)acrylates and the uses thereof.

The prior art contains a method for preparing derivatives of methacrylate compounds based on acetoacetamides and acetoacetates.

Synthesis of C—H acidic monomers based on derivatives of cyanoacetic acid is not possible according to the method described in EP 0013147, although the claim includes this in the description. In EP 0013417, various amino alcohols or diamines and the methacrylate derivatives thereof are reacted with diketene and the corresponding derivatives of acetoacetic acid are obtained thereby. These also represent C—H acidic compounds. However, diketene is not suitable as a starting material for the synthesis of cyanoacetic acid and the carboxylic acid derivatives thereof (esters, amides etc), even just because the carbon skeleton is a C4 body and cyanoacetic acid is a C3 body. In order to synthesize non-symmetrically substituted diamines, EP 0013147 also makes use of protecting group chemistry in order to temporarily block an amine in order to protect it from a reaction. This is not economical and, because of the additional reaction steps, is expensive in terms of process technology.

Carboxylic acid derivatives of acetoacetic acid readily give coloured complexes, which are unsuitable for a wide variety of clearcoat applications.

It was therefore an object to provide a method for preparing C—H acidic (meth)acrylates based on cyanoacetic acid. It was especially an object to prepare a C—H acidic monomer without a 1,3-diketone structure, as in acetoacetic acid.

A further object consisted in providing hydrolysis-stable (meth)acrylates, so as to enable particularly good storage stability in the product.

The objects were achieved by a method for preparing C—H acidic (meth)acrylates by reacting a diamine (B) with $R^2$: $C_nH_mO_xN_y$
where
n=2-15
m=4-30
x=0-4 and
y=0-4
with an ester of cyanoacetic acid (A), in order to form the intermediate product (IP). Most particular preference is given here to using the methyl and ethyl esters (Z=$CH_3$, $C_2H_5$) of cyanoacetic acid, since these are widely commercially available, however higher esters are also readily suitable for the reaction. As by-product in this reaction (as would be expected by those skilled in the art), both amino groups of a diamine react with the cyanoacetic acid to give a bis-cyanoacetamide (BP). This reaction is undesirable, since additional method steps would be required in order to separate off BP, which has a negative influence on the economic viability and costs of the method.

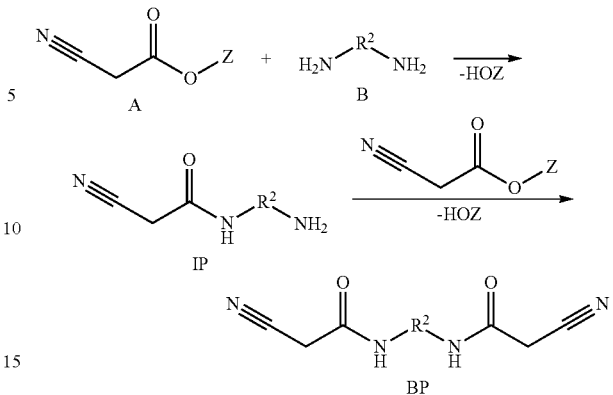

It is simpler to work with an excess of diamine, which also has a lower boiling point than the IP, and can therefore be removed more easily than BP, which is just as temperature-sensitive as IP. Surprisingly, the formation of BP is very greatly suppressed even with small excesses of B, for example with an excess of 1.001:1 and, with an excess of 10:1, particularly preferably 4:1, of B, a crude product of >99% IP is obtained after removing the diamine B. The separation of B can in this case be carried out by extraction or crystallization but especially by distillation, preferably under reduced pressure. The IP obtained after removal of B can be further reacted as a crude product with a (meth) acrylate derivative (MAD) without further work-up. Here, the reaction can proceed with acid halides (c2) (preferably using bases to scavenge the hydrogen halides forming) and also by reaction with esters of (meth)acrylic acid (c1). In this regard, a mixture of dioctyltin oxide (DOTO) and isopropyl titanate (IPT) has proven particularly suitable as catalyst. However, the reaction of BP with the acid anhydrides of (meth)acrylic acid (c2) has been shown to be particularly efficient.

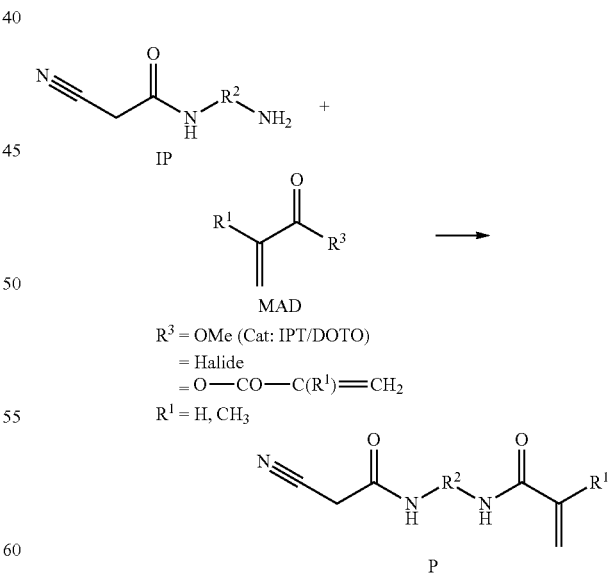

Surprisingly, it has been found that high conversions are achieved, and the amount of by-products is greatly reduced, with the method according to the invention.

The notation "(meth)acrylate" here means both methacrylate, for example methyl methacrylate, ethyl methacrylate, etc., and acrylate, for example methyl acrylate, ethyl acrylate, etc., and mixtures of the two.

Diamines

Suitable diamines are selected from the group of aliphatic, linear or branched or cyclic substituted and unsubstituted diamines and aromatic (ortho, meta or para) substituted diamines.

Particular preference is given to diamines selected from the group of ethylenediamine, 1,3-diaminopropane, 1,4-diaminobutane, 1,5-diaminopentane, 1,6-hexanediamine, 1,7-diaminoheptane, 1,8-diaminooctane, 1,10-diaminodecane, 1,2-diaminopropane, isolated and mixtures of cis and trans isomers of 1,2-diaminocyclohexane, isolated and mixtures of cis and trans isomers of 1,3-diaminocyclohexane, isolated and mixtures of cis and trans isomers of 1,4-diaminocyclohexane, 1,3-diamino-2-hydroxypropane, 2,2-dimethyl-1,3-propanediamine, isolated and mixtures of cis and trans isomers of isophorondiamine, isolated and mixtures of cis and trans isomers of 1,3-cyclohexanebis(methylamine), 4,4'-methylenebis(cyclohexylamine), isolated and mixtures of cis and trans isomers of 4,4'-methylenebis(2-methylcyclohexylamine).

The ratio of alkyl acid anhydride or alkyl acid halide to intermediate product in (c2) is between 0.2:1 and 5:1.

Particular preference is given to reacting at the ratio 0.5:1, since in this case 1 eq. of intermediate product amine neutralizes the acid formed from anhydride or acid halide.

Most particular preference is given to the ratio 1:1, since in this case large portions of the hitherto expensively prepared amine react further to give the product, despite earlier reaction with the carboxylic acid of the anhydride.

It may likewise be preferable to work with an excess of anhydride of >1:1, since this helps to reach full conversion more quickly.

(Meth)Acrylic Anhydride

The intermediate product (IP) in c2) is reacted with (meth)acrylic anhydrides selected from the group of methacrylic anhydride and acrylic anhydride.

Reaction Conditions

The reaction in a is carried out at temperatures between 0-120° C., preferably between 10 and 40° C. during the metering, and at temperatures up to 100° C. in the post-reaction phase and preparation for work-up. In c1, in the range 60-140° C., preferably 100-120° C. In c2, 0-40° C., possibly in the post-reaction up to 100° C.

The reaction time lasts 15 min to 10 h.

In order to avoid the formation of undesirable by-products, the temperature is kept as low as possible and an excess of amine is employed in a.

Neutralization and Work-Up

The intermediate product (IP) can be further used without work-up.

Preferred Method Variants

The intermediate product (IP) from step b is taken up in a solvent while it is still hot, since otherwise it would solidify to a glass, and thus reacts considerably better. Suitable solvents are $H_2O$, MTBE, THF, acetonitrile, dioxane, MAD and alcohols. The selection is obvious for those skilled in the art, based on the respective purpose of the reaction.

In step c2, a solvent is employed selected from the group of $H_2O$, MTBE, THF, acetonitrile, dioxane, MAD and alcohols.

Extraction or Crystallization

The product (P) can be further used without work-up. If required, it can also have all low boilers removed from it under reduced pressure, be recrystallized by addition of a polar solvent, or be extracted by addition of an immiscible solvent.

It was found that the inventive C—H acidic (meth) acrylates are hydrolysis-stable and hence storage-stable for a long period.

The C—H acidic (meth)acrylates have many fields of use. Preference is given to applications in coatings and paints, especially in clearcoats. Likewise, they may be used as polymerizable monomer for preparing polymers which can crosslink with ketones, aldehydes, isocyanates and activated double bonds at room temperature.

The examples given below better illustrate the present invention, without restricting the invention to the features disclosed therein.

EXAMPLES

Example 1: Preparation of N-(2-ethylamino)-2-cyanoacetamide 600 g (10.0 mol) of ethylenediamine are initially charged in a 2 l four-necked round-bottomed flask with sabre stirrer, stirrer motor, thermometer and a 500 ml addition funnel. 248 g (2.5 mol) of methylcyanoacetate are metered in thereto dropwise within 60 minutes, such that the reaction temperature does not exceed 30° C. During this time, the four-necked round-bottomed flask is cooled in an ice-water bath. In the course of the addition of methylcyanoacetate, the reaction mixture becomes increasingly pink coloured, and then lilac. To complete the reaction, the reaction mixture is stirred for a further 90 minutes at room temperature.

Subsequently, the excess ethylenediamine is removed under reduced pressure. For this purpose, the reaction mixture is heated to 100° C. (oil bath temperature) and the volatile constituents are distilled off over a period of 2 hours at a pressure of up to 5 mbar.

The product is obtained as a dark, glass-like solid with a purity of 97.9 area % (determined using GC-RV). The product yield is 309 g (95%).

Comparative Example 1: Preparation of N,N'-ethylenebismethacrylamide

A 40% aqueous solution of ethylenediamine (25.5 g, 0.17 mol) is initially charged in a 250 ml four-necked round-bottomed flask with sabre stirrer, stirrer motor, thermometer and a 100 ml addition funnel. 26 g (0.17 mol) of methacrylic anhydride are metered in thereto within 60 minutes, such that the reaction temperature does not exceed 30° C. During this time, the four-necked round-bottomed flask is cooled in an ice-water bath. In the course of the addition of methacrylic anhydride, a white solid is formed.

The white solid is separated off by filtration, and dried. It is N,N'-ethylenebismethacrylamide with a purity of 74.8 area % (determined using GC-RV). The product yield is 20 g (60%).

Example 2: Preparation of N-(2-cyanoethylamidoethyl)methacrylamide

A mixture of 147 g (1.2 mol) of N-(2-ethylamino)-2-cyanacetamide and 600 g (6.0 mol) of methylmethacrylate are initially charged in a 1 l four-necked round-bottomed flask with air inlet, sabre stirrer, stirrer motor, and a 50 cm-long 29 mm-thick mirrored column with random packing, filled with 6×6 Raschig rings. 7 mg (10 ppm) of 4-hydroxy-2,2,6,6-tetramethylpiperidinooxyl and 0.15 g (200 ppm) of hydroquinone monomethyl ether are added thereto, followed by 7.4 g of a mixture comprising 65.6 wt % of dioctyltin oxide and 34.4 wt % of tetraisopropyl titanate.

The reaction mixture is heated under reflux, with the methanol forming being distilled off as an azeotrope via the column with random packing. After approximately 3.5 hours, the conversion, determined by GC, is 58%.

Example 3: Preparation of N-(2-cyanoethylamidoethyl)methacrylamide 312 g (2.4 mol) of N-(2-ethylamino)-2-cyanoacetamide from example 1 are dissolved in 468 g of water in a 2 l three-necked round-bottomed flask with sabre stirrer, stirrer motor, thermometer and a 500 ml addition funnel. 370 g (2.4 mol) of methacrylic anhydride are slowly added dropwise thereto, with a light brown precipitate being formed. The reaction mixture is then stirred for a further 1.5 hours at 80° C.

The resulting clear, dark red reaction mixture has low boilers removed therefrom under reduced pressure, is concentrated down to 646 g, and has 400 g of isopropanol added thereto. This leads to the formation of a precipitate which is separated off by filtration.

The product is obtained as a brown, crystalline solid with a purity of 77.0 area % (determined using GC-RV). The product yield is 346 g (73.9%).

Example 4: Preparation of N-(2-butylamino)-2-cyanoacetamide 353 g (4.0 mol) of 1,4-diaminobutane are melted at approximately 30° C. in a 1 l four-necked round-bottomed flask with sabre stirrer, stirrer motor, thermometer and a 250 ml addition funnel. 99 g (1.0 mol) of methylcyanoacetate are metered in dropwise thereto within 30 minutes, such that the reaction temperature remains at approximately 30° C. to 40° C. During this time, the four-necked round-bottomed flask is cooled in an ice-water bath. In the course of the addition of methylcyanoacetate, the reaction mixture becomes increasingly intensely yellow coloured. To complete the reaction, the reaction mixture is stirred for a further 90 minutes at room temperature, with the reaction mixture becoming red coloured.

Subsequently, excess 1,4-diaminobutane is removed under reduced pressure. For this purpose, the reaction mixture is heated to 100° C. (oil bath temperature) and the volatile constituents are distilled off over a period of 2.5 hours at a pressure of up to 2 mbar.

The product is obtained as a dark, glass-like solid with a purity of 89.1 area % (determined using GC-RV). The product yield is 146 g (84%).

Example 5: Preparation of N-(2-cyanoethylamidobutyl)methacrylamide 360 g (0.93 mol) of N-(2-butylamino)-2-cyanoacetamide from example 4 are dissolved in 540 g of water in a 1 l four-necked round-bottomed flask with sabre stirrer, stirrer motor, thermometer and a 500 ml addition funnel and cooled to 0° C. in an ice-water bath. 143 g (0.93 mol) of methacrylic anhydride, dissolved in 300 ml of methanol, are slowly added thereto dropwise. Subsequently, the reaction mixture is stirred overnight at room temperature, with the reaction mixture becoming green coloured.

The reaction mixture was concentrated under reduced pressure at 80° C. and 35 mbar to 263 g. The residue is dissolved in 160 g of isopropanol and the resulting solution is stored at room temperature. This leads to the formation of a precipitate which is separated off by filtration.

The product is obtained as a yellow crystalline solid. The purity is approximately 94.0 area % (determined using GC-RV).

Example 6: Preparation of N-(2-hexylamino)-2-cyanoacetamide 465 g (4.0 mol) of 1,6-diaminohexane are melted at approximately 41° C. in a 1 l four-necked round-bottomed flask with sabre stirrer, stirrer motor, thermometer and a 250 ml addition funnel. 99 g (1.0 mol) of methylcyanoacetate are metered in thereto dropwise within 30 minutes, such that the reaction temperature remains at approximately 50° C. to 75° C. In the course of the addition of methylcyanoacetate, the reaction mixture becomes increasingly intensely yellow coloured. To complete the reaction, the reaction mixture is stirred for a further 90 minutes at approximately 50° C. to 75° C., with the reaction mixture becoming red coloured.

Subsequently, the excess 1,6-diaminohexane is removed under reduced pressure. For this purpose, the reaction mixture is heated to 120° C. (oil bath temperature) and the volatile constituents are distilled off over a period of 4 hours at a pressure of up to 2 mbar.

The product is obtained as a dark, glass-like solid with a purity of approximately 100 area % (determined using GC-RV). The product yield is 172 g (94%).

Example 7: Preparation of N-(2-cyanoethylamidobutyl)methacrylamide 31 g (0.2 mol) of methacrylic anhydride and 150 g of water are initially charged in a 1 l four-necked round-bottomed flask with sabre stirrer, stirrer motor, thermometer and a 500 ml addition funnel and cooled to 0° C. in an ice-water bath. 360 g (0.93 mol) of N-(2-hexylamino)-2-cyanoacetamide from example 6 are dissolved in 3240 g of methanol at 60° C. and cooled to room temperature. This solution is added over a period of 30 minutes via the addition funnel to the methacrylic anhydride. The reaction temperature is kept below 20° C. The reaction mixture is then stirred for a further 3 hours at room temperature.

The product formed is detected in the reaction mixture using GC-RV and can be isolated by crystallization from isopropanol.

Analysis

Gas chromatography (GC)

Instrument: 7820A from Agilent Technologies

Column: DB5, 30 m, ø 0.250 mm, 0.25 μm film

Temperature Program:

Injection at 60° C., then hold for 2 min. Subsequently heat to 240° C. at 20° C./min and after reaching that temperature, hold at 240° C. for 8 min.

The invention claimed is:
1. A method for preparing C—H acidic (meth)acrylates of formula (I):

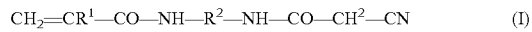

(P)

wherein:
R$^1$ is H or methyl;
R$^2$ is C$_n$H$_m$O$_x$N$_y$;

wherein:

n=2-15;

m=4-30;

x=0-4; and y=0-4;

wherein said method comprises:
a) reacting an ester of cyanoacetic acid (A) with a diamine (B) in excess;
b) removing unreacted diamine (B) from the reaction solution to obtain the intermediate product (IP), an amino-functionalized cyanoacetamide;
c) obtaining product (P) by reacting intermediate product (IP) obtained in step b) with either:
c1) (meth)acrylic acid esters (MAD); or
c2) (meth)acrylic anhydride (MAD) or (meth)acryloyl halide (MAD);
d) optionally isolating (P) by extraction or crystallization.

2. The method of claim 1, wherein the ester of cyanoacetic acid is selected from the group consisting of: of methyl cyanoacetate; and ethyl cyanoacetate.

3. The method of claim 1, wherein the diamine is an aliphatic, linear or branched or cyclic substituted or unsubstituted diamine; or an aromatic (ortho, meta or para) substituted diamine.

4. The method of claim 1, wherein the excess of diamine to ester of cyanoacetic acid is between 10:1 and 1.001:1.

5. The method of claim 1, wherein unreacted diamine in step b) is removed by means of distillation, extraction or crystallization.

6. The method of claim 1, wherein the reaction of the intermediate product in c1) is carried out with esters selected from the group consisting of: methyl (meth)acrylate; ethyl (meth)acrylate; butyl (meth)acrylate; ethyl acrylate; butyl acrylate; and higher alcohols of (meth)acrylate.

7. The method of claim 1, wherein the intermediate product in c2) is reacted with alkyl acid halides selected from the group consisting of: (meth)acryloyl bromides; and (meth)acryloyl chlorides.

8. The method of claim 1, wherein the intermediate product in c2) is reacted with (meth)acrylic anhydrides selected from the group consisting of: methacrylic anhydride; and acrylic anhydride.

9. The method of claim 1, wherein the reaction of an ester of cyanoacetic acid with a diamine takes place at temperatures between −20° C. and 140° C.

10. The method of claim 1, wherein the reaction of an ester of cyanoacetic acid with a diamine takes place at temperatures between 0° C. and 30° C.

11. The method of claim 1, wherein the ratio of alkyl acid esters to intermediate product in c1) is between 1.01:1 and 20:1.

12. The method according of claim 1, wherein the ratio of alkyl acid anhydride or alkyl acid halide to intermediate product in c2) is between 0.2:1 and 5:1.

* * * * *